United States Patent [19]

Millington

[11] 4,215,103
[45] Jul. 29, 1980

[54] METHOD FOR PRODUCING A PREPARATION FOR DIAGNOSTIC RADIOLOGY AND APPARATUS THEREFOR

[75] Inventor: Arthur R. Millington, Blackburn, England

[73] Assignee: Linton Medical Services Limited, Blackburn, England

[21] Appl. No.: 874,154

[22] Filed: Feb. 1, 1978

[30] Foreign Application Priority Data

Feb. 2, 1977 [GB] United Kingdom ................ 4319/77

[51] Int. Cl.² .................... B61K 29/02; A67D 5/62
[52] U.S. Cl. .................... 424/4; 222/146 C; 222/190; 222/251; 252/305; 424/5; 424/43
[58] Field of Search ............... 424/4, 5, 43; 252/305; 222/190, 251, 146 C

[56] References Cited

U.S. PATENT DOCUMENTS

| | | | |
|---|---|---|---|
| 2,193,897 | 3/1940 | Bobrick | 222/190 X |
| 2,205,147 | 6/1940 | Madsen | 222/190 X |
| 2,726,017 | 12/1955 | Burden | 222/190 X |
| 3,235,462 | 2/1966 | Wolfson | 424/4 |
| 3,281,014 | 10/1966 | Nickerson | 222/190 X |
| 3,689,630 | 9/1972 | Kikuchi et al. | 424/4 |
| 3,956,476 | 5/1976 | Daigo et al. | 424/4 |

FOREIGN PATENT DOCUMENTS

| | | | |
|---|---|---|---|
| 43-11288 | 5/1968 | Japan | 424/4 |
| 49-46054 | 12/1968 | Japan | 424/4 |

OTHER PUBLICATIONS

Pochaczevsky, Technical Notes, vol. 167, pp. 461–462, May 1973.
Orth et al., Technical Notes, pp. 530–532, Feb. 1977.

*Primary Examiner*—Norman Morgenstern
*Assistant Examiner*—Vera C. Clarke
*Attorney, Agent, or Firm*—Fleit & Jacobson

[57] ABSTRACT

A diagnostic radiology preparation for injestion by patients, which preparation comprises a radio opaque substance such as barium sulphate, a carrier such as water and a dissolved and/or absorbed gas such as carbon dioxide. The gas is present in an amount such that it is released when the preparation is ingested.

9 Claims, 1 Drawing Figure

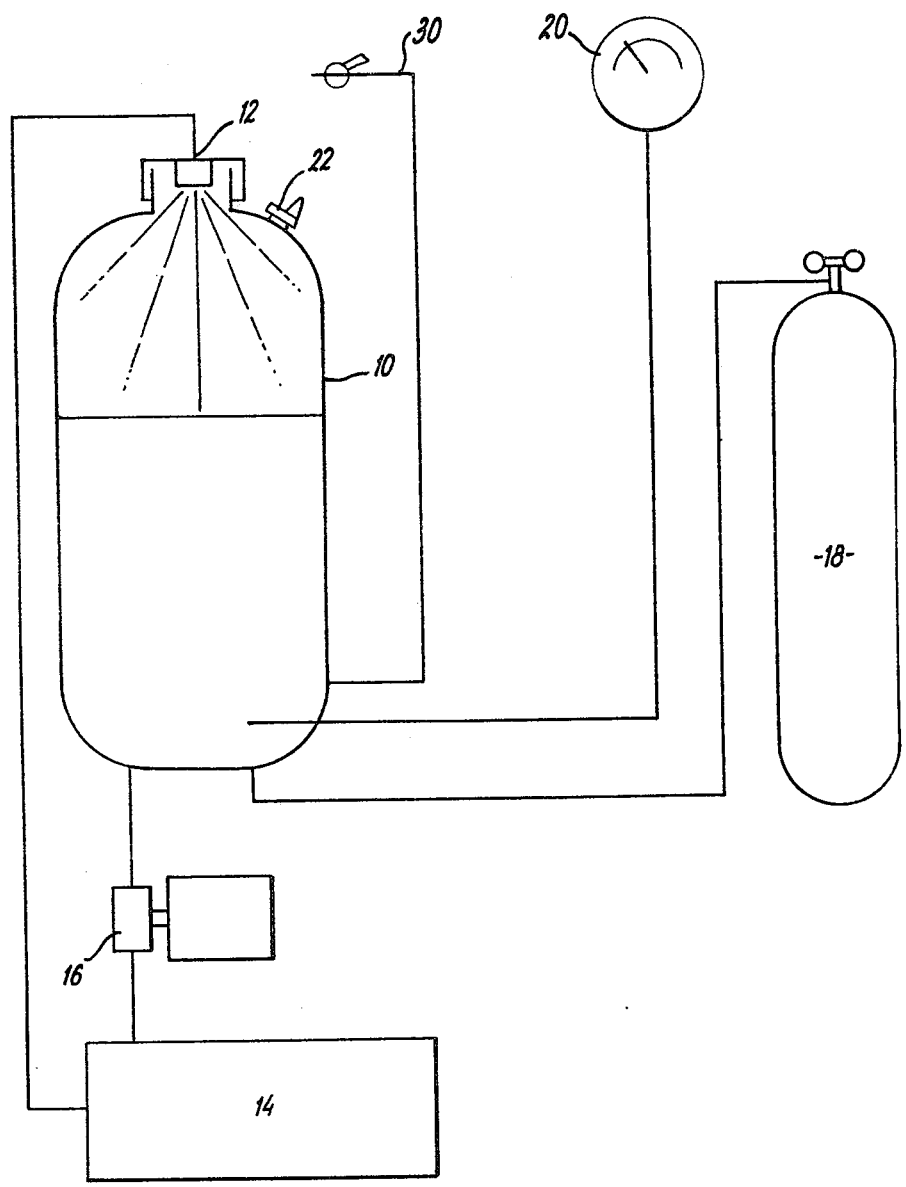

METHOD FOR PRODUCING A PREPARATION FOR DIAGNOSTIC RADIOLOGY AND APPARATUS THEREFOR

This invention relates to a preparation for diagnostic radiology and a method and apparatus for producing such preparation.

Recent investigations into the effectiveness of radiological examination of lesions in the upper gastro intestinal tract have revealed that the conventional barium metal taken by the patient prior to such examination does not enable small lesions, such as shallow ulcers, and flat or surface ulcers, to be detected. Additionally, it has been found that the conventional barium metal cannot reliably be counted on to enable any difference between benign and malignant ulcers to be noted.

In order to deal with this problem proposals have been made for expanding or distending the part under examination by introducing into the intestine pellets or tablets which release carbon dioxide. An alternative proposal comprises introducing air to the desired location in the intestine by means of a tube. However, neither of these techniques is entirely satisfactory.

According to the present invention there is provided a preparation for diagnostic radiology comprising a radio opaque substance, a carrier and gas in concentration sufficient to cause release of said gas when said preparation is ingested by a patient.

The gas employed in the invention is preferably carbon dioxide. However, any other gas or mixture of gases can be used provided it is not harmful to the patient, for example a mixture of equal volumes of carbon dioxide and nitrogen.

The concentration of gas can be varied within the limitation that there must be sufficient present to be released when the preparation is ingested. Generally from three to four parts of gas per part of preparation by volume is found to give good results.

The constituents of the preparation, into which the gas is incorporated are known per se and are selected in accordance with the mixture of the particular diagnosis to be performed. Generally however, the radio opaque substance is barium sulphate and the carrier is water. If desired, additives such as anti-foaming agents can be included in the preparation in order to prevent or reduce the effect of any foam, formed when gas is released, on radiological examination.

The invention also provides a method of producing a preparation as defined above comprising incorporating gas in a preparation in a concentration sufficient to cause release of said gas when the preparation is ingested by a patient.

Preferably the step of incorporating the gas in the preparation is carried out at reduced temperature and/or elevated pressure. It is also preferred that the surface area of preparation brought into contact with the gas be as large as possible.

The invention also provides apparatus for producing a preparation as defined above comprising a pressure vessel, means for admitting preparation to the vessel, means for admitting to the vessel gas to be incorporated in the preparation, means for cooling the gas/preparation mixture to cause the gas to be incorporated in the preparation and means for regulating the pressure in the vessel.

In this specification reference is made to the gas being incorporated in the preparation. This term is intended to include both gas which is dissolved in the preparation which will acount for all or the bulk of the incorporated gas and also which may be included in some other way for example by adsorption onto the surface of the solids in the preparation.

A specific embodiment of the invention will now be described by way of example with reference to the accompanying drawing which shows diagrammatically one form of apparatus for making a preparation according to the invention.

Referring to the drawing a pressure vessel 10 is provided with an inlet 12 in the form of a spray at the top thereof. The inlet 12 is connected to the bottom of the vessel through cooling means 14 and a pump 16. A container 18 of carbon dioxide gas under pressure is also connected to the bottom of the vessel 10.

The vessel is also fitted with a temperature measuring means 20 and pressure regulator 22.

In order to make a preparation according to the invention the vessel 10 is partially filled with a preparation known per se for example a barium preparation. Carbon dioxide gas is admitted to the vessel 10 from the container 18, air in the vessel being vented through regulator 22. When the vessel contains the predetermined quantities of barium preparation and gas the pump is switched on and the contents of the vessel cycled through the cooling means 14 and the spray 12 until the desired level of dissolved gas is attained. The resulting preparation can then be drawn for use from the vessel through line 30.

Most radio opaque substances, including barium sulphate tend to settle out from diagnostic radiology preparations. In order to combat that it is desirable that the preparation be thoroughly mixed at least prior to use. Such mixing is achieved in the apparatus just described by the agitation imparted during cycling of the preparation through the cooling means and spray. However agitation to produce uniform or substantially uniform distribution of the radio opaque substance in the preparation may be produced by other means such as a paddle disposed in the vessel.

The concentration of dissolved gas, as stated depends on both pressure and temperature. For example, using the above described apparatus and holding the pressure constant at 40 p.s.i.g. the amount of dissolved gas varies with temperature as illustrated by the following figures.

| Temperature °F. | Parts by volume dissolved gas/part by volume of preparation |
|---|---|
| 40 | 5.1 |
| 45 | 4.7 |
| 50 | 4.3 |
| 55 | 3.9 |
| 60 | 3.6 |
| 65 | 3.3 |
| 70 | 3.1 |
| 75 | 2.9 |
| 80 | 2.6 |
| 85 | 2.45 |
| 90 | 2.3 |
| 95 | 2.15 |
| 100 | 2 |

The following Examples further illustrate the invention.

EXAMPLE 1

A proprietory barium sulphate preparation sold under the Trade Mark "Micropaque" and which contains from 56.8 to 57.8 % wt/wt of barium sulphate was gasified with carbon dioxide using the apparatus of the kind described above. A quantity of Micropaque containing 100 g solids was placed in the apparatus, the pressure adjusted to 20 p.s.i.g. and the temperature held at 5° C. The gas uptake was found to be 524 ml. The process was repeated a further five times and the gas uptake found to be 540 ml, 534 ml, 538 ml, 578 ml, 590 ml the average gas uptake being 551 ml against a theoretical gas uptake of 265 ml.

EXAMPLE 2

The same procedure was followed as in Example 1 except that the temperature was raised to 15° C. The gas uptake in five repeated processes was found to be 386 ml, 576 ml, 517 ml, 517 ml and 540 ml giving an average gas uptake of 507 ml against a theoretical gas uptake of 200 ml.

EXAMPLE 3

The same procedure was followed as in Example 2 except that the gas was changed to a gas mixture of equal volume of $CO_2$ and $N_2$. Gas uptake found in four repeated processes was 246 ml, 243 ml, 228 ml, and 231 ml giving an average gas uptake of 237 ml against a theoretical gas uptake of 100 ml.

EXAMPLE 4

The procedure employed in Example 1 was followed but with the pressure raised to 40 p.s.i.g. The process was repeated six times to give gas uptake figures of 692 ml, 694 ml, 711 ml, 543 ml, 654 ml, and 561 ml, the average gas uptake being 642 ml against a theoretical gas uptake of 420 ml.

EXAMPLE 5

The procedure of Example 4 was followed using a different batch of "Micropaque". Four repeats of the process gave gas uptake figures of 460 ml, 461 ml, 470 ml and 464 ml, the average gas uptake being 464 ml.

EXAMPLE 6

The same procedure was followed as in Example 2 but with the pressure raised to 40 p.s.i.g. The process was carried out twice and the gas uptake on both occasions was found to be 689 ml against a theoretical gas uptake of 315 ml.

EXAMPLE 7

The procedure of Example 6 was followed using a different batch of "Micropaque" (the same batch as employed in Example 5). Gas uptake figures obtained were 402 ml, 404 ml, 409 ml, 418 ml, 417 ml and 413 ml the average being 410 ml.

EXAMPLE 8

A proprietory dry barium sulphate preparation sold under the Trade Mark "E-Z Paque" was mixed with water to form a 53% w/w dispersion. A quantity of the dispersion containing 100 g solids was gasified with $CO_2$ at 5° C. at 20 p.s.i.g. The process was repeated twelve times and the gas uptake found to be as follows: 375 ml, 376 ml, 385 ml, 379 ml, 417 ml, 411 ml, 386 ml, 363 ml, 330 ml, and 367 ml respectively, the average being 379 ml against a theoretical gas uptake of 323 ml.

EXAMPLE 9

The same procedure was followed as in Example 8 except that the temperature was 15° C. The process was repeated eight times to give gas uptake figures in ml of 264, 265, 254, 266, 279, 280, 280 and 279, the average being 271 ml against a theoretical gas uptake of 232 ml.

EXAMPLE 10

The same procedure was followed as in Example 8 except that the pressure was 40 p.s.i.g. The process was repeated six times to give gas uptake figures in ml of 495, 494, 525, 540, 506, and 508, the average being 511 ml against a theoretical gas uptake of 510 ml.

EXAMPLE 11

The same procedure was followed as in Example 10 except that the dispersion was made up as 56% w/w. The process was repeated six times to give gas uptake figures, in ml, of 423, 448, 480, 486, 454, and 457, the average being 458 ml against a theoretical gas uptake of 451 ml.

EXAMPLE 12

The same procedure was followed as in Example 10 except that the dispersion was made up as 72% w/w. The process was repeated six times to give gas uptake figures, in ml, of 346, 259, 252, 272, 248 and 280, the average being 276 ml against a theoretical gas uptake of 224 ml.

EXAMPLE 13

The same procedure was followed as in Example 9 except that the procedure was 40 p.s.i.g. The process was repeated eight times to give gas uptake figures, in ml, of 338, 445, 343, 332, 371, 409, 421 and 346, the average being 375 ml against a theoretical gas uptake of 366 ml.

EXAMPLE 14

A proprietory dry barium sulphate preparation marketed as "Baritop G" was mixed with water to form a 64.0% w/w dispersion. A quantity of the dispersion containing 100 g solids was gasified with $CO_2$ at a temperature of 5° C. and pressure of 20 p.s.i.g. The process was repeated six times to give gas uptake figures, in ml, of 254, 253, 248, 247, 251 and 255, the average being 251 ml against a theoretical gas uptake of 205 ml.

EXAMPLE 15

The procedure of Example 14 was followed but with the temperature at 15° C. The process was repeated six times giving gas uptake, in ml, of 185, 187, 182, 182, 193 and 193, the average being 187 ml against a theoretical gas uptake of 147 ml.

EXAMPLE 16

The same procedure was followed as in Example 14 except that the gas was a mixture of equal volumes of $CO_2$ and $N_2$. The process was repeated six times, the gas uptake figures being, in ml, 137, 138 144, 143, 140 and 141, average 140 ml against a theoretical gas uptake of 102 ml.

EXAMPLE 17

The procedure of Example 14 was followed but with the pressure adjusted to 40 p.s.i.g. The process was repeated six times, the gas uptake figures, the ml, being 340, 346, 319, 322, 330 and 344, the average being 334 ml against a theoretical gas uptake of 323 ml.

EXAMPLE 18

The procedure of Example 15 was followed but with the pressure adjusted to 40 p.s.i.g. The process was repeated four times and the gas uptake figures, in ml, were 270, 269, 288 and 289, the average being 279 ml against a theoretical gas uptake of 232 ml.

EXAMPLE 19

The same procedure was followed as in Example 16 but with the pressure adjusted to 40 p.s.i.g. The process was repeated six times and the gas uptake figures were, in ml, 194, 195, 203, 199, 202 and 196 the average being 198 ml against a theoretical gas uptake of 161 ml.

What is claimed is:

1. A method of producing a preparation for diagnostic radiology, the preparation, when taken into the body of a user, releasing a gas that expands within the body of a user, comprising:
    placing a mixture containing a radio opaque substance and a carrier in a pressure vessel, the radio opaque substance being present in a quantity sufficient for diagnostic radiology;
    adding a non-toxic gas to the pressure vessel; and
    cycling the gas and mixture for a period of time sufficient to obtain a predetermined level of dissolved gas within the mixture, the level being sufficient to cause release of the gas within the body of a user.

2. A method according to claim 1, wherein the cycling includes cooling the gas and mixture.

3. A method according to claim 1, wherein the cycling includes spraying the mixture into the pressure vessel through an inlet in the top thereof.

4. A method according to claim 1, including removing air from the container while the gas is being added to the container.

5. An apparatus for producing a preparation for diagnostic radiology comprising:
    vessel means for defining a pressure vessel;
    means for adding a mixture of a radio opaque substance and a carrier into said vessel means, the radio opaque substance being present in a quantity sufficient for diagnostic radiology;
    means for adding a non-toxic gas to said vessel means; and
    means for cycling the mixture and gas so that a preparation having a predetermined level of gas dissolved therein is produced, the level being sufficient to cause release of the gas within the body of a user.

6. An apparatus according to claim 5, wherein the pressure vessel has an inlet in a top thereof and wherein the means for cycling includes means positioned in said inlet for spraying the mixture into the pressure vessel.

7. An apparatus according to claim 5, wherein the means for cycling includes means for cooling the mixture and gas.

8. An apparatus according to claim 5, further comprising means for controlling the pressure within said pressure vessel.

9. An apparatus according to claim 8, wherein said means for controlling the pressure includes means for removing air from said pressure vessel as gas is being added.

* * * * *